(12) United States Patent
Euzen et al.

(10) Patent No.: US 9,014,805 B2
(45) Date of Patent: Apr. 21, 2015

(54) ACTIVE IMPLANTABLE MEDICAL DEVICE TYPE SUCH AS A PACEMAKER WITH CAPTURE TEST BY ANALYSIS OF A VECTOGRAM

(71) Applicant: Sorin CRM S.A.S., Clamart Cedex (FR)

(72) Inventors: Marie-Anne Euzen, Bievres (FR); Elodie Vincent, Antony (FR)

(73) Assignee: Sorin CRM S.A.S., Clamart (FR)

( * ) Notice: Subject to any disclaimer, the term of this patent is extended or adjusted under 35 U.S.C. 154(b) by 0 days.

(21) Appl. No.: 14/105,868

(22) Filed: Dec. 13, 2013

(65) Prior Publication Data

US 2014/0172036 A1 Jun. 19, 2014

(30) Foreign Application Priority Data

Dec. 14, 2012 (FR) ...................................... 12 62073

(51) Int. Cl.
| | | |
|---|---|---|
| *A61N 1/00* | (2006.01) | |
| *A61N 1/37* | (2006.01) | |
| *A61B 5/04* | (2006.01) | |
| *A61B 5/0464* | (2006.01) | |
| *A61N 1/368* | (2006.01) | |
| *G06K 9/00* | (2006.01) | |
| *A61B 5/00* | (2006.01) | |

(52) U.S. Cl.
CPC ............. *A61N 1/3712* (2013.01); *A61B 5/7264* (2013.01); *A61B 5/04011* (2013.01); *A61B 5/0464* (2013.01); *A61N 1/3684* (2013.01); *A61N 1/371* (2013.01); *G06K 9/0055* (2013.01)

(58) Field of Classification Search
CPC ....... A61N 1/371; A61N 1/361; A61N 1/362; A61N 1/365; A61N 1/368
USPC .......................................................... 607/18
See application file for complete search history.

(56) References Cited

U.S. PATENT DOCUMENTS

| 5,411,533 A | 5/1995 | Dubreuil et al. |
|---|---|---|
| 2006/0253164 A1 | 11/2006 | Zhang et al. |
| 2011/0118804 A1* | 5/2011 | Henry et al. ..................... 607/28 |

FOREIGN PATENT DOCUMENTS

| EP | 1 080 744 A1 | 3/2001 |
|---|---|---|
| EP | 1 287 849 A1 | 3/2003 |
| EP | 1 995 685 A2 | 11/2008 |
| EP | 2 324 885 A1 | 5/2011 |
| WO | WO-93/02741 A1 | 2/1993 |

OTHER PUBLICATIONS

Preliminary Search Report for French Patent Application No. 1262073, dated Jul. 4, 2013, 2 pages.

* cited by examiner

*Primary Examiner* — Robert N Wieland
(74) *Attorney, Agent, or Firm* — Foley & Lardner LLP

(57) ABSTRACT

A device produces at least two distinct temporal components ($V_{bip}$, $V_{uni}$) from two separate endocardial electrogram (EGM) signals concurrently collected. The capture test determines a non-temporal 2D characteristic (VGM) representative of the cardiac cycle to be analyzed. The VGM is constructed using variations of one of the temporal components ($V_{uni}$) according to the other ($V_{bip}$). The devices determines the presence or absence of capture by analysis of this characteristic relative to a two dimensional domain.

20 Claims, 4 Drawing Sheets

ACTIVE IMPLANTABLE MEDICAL DEVICE TYPE SUCH AS A PACEMAKER WITH CAPTURE TEST BY ANALYSIS OF A VECTOGRAM

CROSS-REFERENCE TO RELATED APPLICATION

This application claims the benefit of and priority to French Patent Application No. 1262073, filed Dec. 14, 2012, which is incorporated herein by reference in its entirety.

BACKGROUND

The invention relates to "active implantable medical devices" as defined by Directive 90/385/EEC of 20 Jun. 1990 the Council of the European Communities, specifically implants to continuously monitor cardiac rhythm and deliver if necessary to the heart electrical pulses for stimulation, resynchronization and/or defibrillation in case of arrhythmia detected by the device.

Antibradycardia pacing involves the controlled delivery of pulses to the atrium and/or the ventricle. This can be accomplished using single or dual chamber devices. In the case of cardiac resynchronization therapy (CRT), stimulation must also be applied to the two ventricles in conjunction (multisite device). In general, after stimulation of a cavity, it is important to collect the "evoked wave," that is to say, the wave of depolarization induced by the stimulation of this cavity, to determine whether the stimulation has been effective or not. This test ("capture test") is used in particular for adjusting the amplitude and/or the width of the stimulation pulses, that is to say, the energy delivered to the stimulation site.

There are many techniques to perform this capture test. Some are described in WO 93/02741A1 or U.S. Pat. No. 5,411,533 A (ELA Medical). One technique is to conduct the stimulation effectiveness threshold test at regular intervals, e.g., every six hours, by implementation of an automatic test algorithm. The amplitude of the stimulation pulse is then adjusted based on the measured threshold and with an extra margin of safety, to take into account uncertainties in the determination of the threshold.

EP1287849 A1 (ELA Medical) discloses a "cycle to cycle" adjustment technique, which includes conducting the capture test and the possible adjustment of the stimulation energy. This technique includes checking at regular intervals (e.g., every six hours) and also continuously checking at each cycle if the stimulation was effective or not.

EP2324885 A1 (Sorin CRM) analyzes endocardial electrogram signals (EGM signals) concurrently collected on two distinct channels taking signals from the same cavity. The two different EGM channels may in particular be that of a unipolar signal (remote or far-field signal collected between the housing and a distal or proximal electrode of the lead), and that of a bipolar signal (close or near-field signal collected between a distal electrode and a proximal electrode of this same lead). Analysis of these signals is a two-dimensional analysis from the "cardiac loop" or "vectogram" (VGM), which is the two-dimensional space representation of one of these two signals relative to the other. This space is typically a "Unipolar channel (y-axis) versus bipolar channel (x-axis)" space, each beat or significant fraction of beat being then represented by its vectogram in the plane thus defined; and therefore ignoring the temporal dimension.

A "vectogram" (VGM), which is obtained from electrogram signals (EGM) from intracardiac leads, is distinct from a "vectocardiogram" (VCG), which is obtained from electrocardiogram signals (ECG) delivered from external electrodes located on the patient's chest.

The analysis of the vectogram for the capture test may be an analysis of the cardiac loop properties. For example, the algorithm calculates and analyzes the descriptor parameters of the vectogram, which may include the angles of the respective tangent vectors considered at various points of the 2D characteristic, or the curvature of this 2D characteristic, or a combination of several parameters, such as a combination of the norm and the angle of the tangent vectors.

Preferably the vectogram analysis is a comparative analysis including a correlation between, first, the characteristics of the vectogram of the cycle to be analyzed, and, second, the same characteristics collected on one or more reference cycles obtained in completely determined conditions: capture, no capture, fusion, etc. For example, the tangent vectors obtained for a cardiac cycle to be analyzed may be compared to the same vectors observed for reference curves, previously obtained, in an identical period, in respectively situations of capture or no capture. Such a characterization algorithm may evaluate a correlation coefficient between the descriptor parameters of the cycle to be analyzed and the reference cycles. The algorithm may discriminate between capture and loss of capture according to the results of the correlation calculation. Such correlation calculations may be combined with other decision criteria, such as the average angle between the respective analyzed vectogram tangent vectors and the reference vectogram. This technique is particularly effective for atypical cycles as in fusion situations, wherein stimulation is initiated concomitantly with spontaneous depolarization during the capture test.

Such a correlation based method is not without drawbacks, however. A first drawback is the level of hardware or software resources necessary for the implementation of the vectogram characterization algorithm. The computational requirements are difficult to reconcile with what is possible to have in a conventional implant, the processor and memory of which are solicited for the implementation of many detection and calculation functions.

A second drawback is the need to have several reference vectograms on which the correlation calculation with the current analysis vectogram is performed. These reference vectograms are obtained either manually, by a test triggered by the practitioner who then validates each reference type (full capture on all stimulated sites, partial capture of certain sites only, total loss of capture, etc.) or automatically. In the case wherein reference vectograms are automatically set, the device regularly performs (e.g., every 4 hours, every week, etc.) high energy stimulation tests or zero volts stimulation tests on the different sites, so as to update the reference vectograms.

SUMMARY

One embodiment of the invention relates to examining the generated vectograms relative to a predetermined range. The generated vectograms can be analyzed, for example, with respect to a rectangular area of predefined size and position. A topological analysis of the distribution of points of the vectogram can be completed relative to the rectangular area. The position of points inside or outside the predetermined domain may be the criteria used to determine the presence or absence of a capture.

One embodiment of the invention relates to a device for delivering electrical stimulation pulses applied to electrodes implanted in at least one cavity of the heart of a patient. The device can collect the electrical activity of the heart. The device can generate at least two distinct temporal components from two distinct signals of endocardial electrogram (EGM) concurrently collected. The device can include a capture test circuit for detecting the occurrence of a depolarization wave induced by the stimulation of the cavity on at least a stimulated cycle. The capture test circuit can determine a representative 2D non-temporal characteristic of the cardiac cycle to be analyzed by pairing the variations of one of the distinct signals' temporal components relative to the other. The capture test circuit can discriminate between the presence or absence of capture by analysis of the non-temporal 2D characteristic.

The capture test circuit can conduct a topological analysis to determine whether the non-temporal 2D characteristic (VGM) is included or not in a predetermined area (D) defined with reference to the space of two temporal components. The capture test circuit can determine that there has been absence of capture when the VGM is not within the predetermined area. The capture test circuit can determine that there has been presence of capture when the VGM is within the predetermined area.

According to various embodiments:

The area can be a rectangular area;

The area can be centered on the point of origin of the reference corresponding to the space of the two temporal components;

The non-temporal 2D characteristic is a 2D sampled characteristic described by a series of successive discrete points, and the topological analysis means analyzes the relative position of each point relative to the two dimensional domain;

The topological analysis may include determining that the 2D characteristic is not included in the domain when at least one point on the 2D sampled characteristic is outside the domain;

In other embodiments, the topological analysis may consider whether two or more points, (e.g., two consecutive points) of the 2D sampled characteristic are outside the domain;

The non-temporal 2D characteristic may be determined for a plurality of successive cardiac cycles, and the topological analysis may decide that there is no capture when at least one of the characteristics thus determined is included in the domain;

The non-temporal 2D characteristic may be determined using a characteristic from the variations of the temporal components on a portion of the cardiac cycle to be analyzed, in an analysis temporal window opened at the moment of stimulation or shifted from that moment, so as to isolate the QRS complex of the heart beat of the ventricular and/or atrial pacing peaks that precede it;

The EGM signals concurrently collected on distinct respective channels may include a bipolar component near-field signal collected between a proximal electrode and a distal electrode of a lead placed in a cardiac cavity, and a unipolar component far-field signal collected between the housing of the device and the proximal or distal lead electrode.

In an exemplary embodiment, a device produces at least two distinct temporal components ($V_{bip}$, $V_{uni}$) from two separate endocardial electrogram (EGM) signals concurrently collected. The capture test is to determine a non-temporal 2D characteristic (VGM) representative of the cardiac cycle to be analyzed, from the variations of one of the temporal components ($V_{uni}$) according to the other ($V_{bip}$); and to determine the presence or absence of capture by analysis of this characteristic. A predetermined domain is defined based on the space of the two temporal components, and a topological analysis determines whether the non-temporal 2D characteristic is included or not in the domain and decides i) the absence of a capture in the first case and ii) the presence of a capture in the second case.

An embodiment of the invention relates to a computerized method for monitoring effective electrical stimulation of a tissue. The method includes simultaneously collecting data for at least two electrical signals using electrodes separately located relative to the tissue. The method further includes creating a series of pairs by temporally matching the data for the at least two electrical signals. The method also includes evaluating the series of pairs relative to a boundary defining a two dimensional area and outputting a presence of capture in response to the evaluation. The tissue may be the heart. The electrodes may be on intracardiac leads. The computerized method may be executed by an active implantable medical device configured to monitor stimulation of the heart. The at least two electrical signals may include two separate endocardial electrogram (EGM) signals. The two separate EGM signals may include (a) a unipolar signal representing a far-field voltage between the housing of the implantable medical device and an electrode; and (b) a bipolar signal representing a near field voltage between a first electrode and a second electrode. The electrode used to collect the unipolar signal may be one of the first electrode and the second electrode. The two dimensional area may be a rectangular area of predefined size and position relative to the series of pairs if plotted. The evaluation may include a topological analysis of the distribution of the series of pairs relative to the area.

DETAILED DESCRIPTION

The invention may be implemented by programming of the control software of a stimulator device, for example, a cardiac pacemaker, resynchronizer and/or defibrillator. The device may include a programmable circuit (e.g., processor) for acquiring a signal provided by endocardial leads and/or one or more implanted sensors.

These devices may include a programmable microprocessor circuitry to receive, format and process electrical signals collected by implantable electrodes, and to deliver stimulation pulses to these electrodes. The software for completing the methods described herein may be downloaded to the implantable device by telemetry software that is stored in memory. The computer code stored in memory may be executed to implement the functions of the invention that are described below.

The invention can particularly be applied to implantable devices such as those of the Reply and Paradym product families produced and marketed by Sorin CRM, Clamart, France.

The method of the invention can be implemented by software, using appropriate algorithms executed by a microcontroller or digital signal processor of a circuit.

The invention includes attempting to detect the evoked wave following the stimulation of a heart cavity from electrogram signals (EGM) collected on two separate channels and analyzed in two dimensions.

Figure 1:
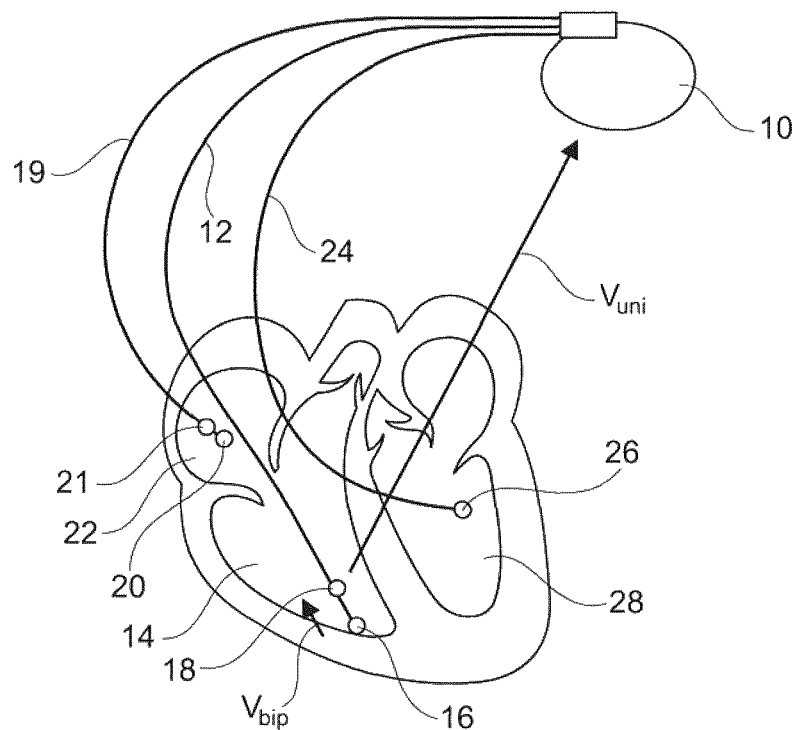
FIG. 1 is a diagram showing a bipolar lead implanted at the apex of the right ventricle of the heart, according to an exemplary embodiment.

FIG. 1 illustrates a stimulation configuration wherein a pulse generator 10 is associated with a lead 12 implanted in the right ventricle 14. The lead head includes two electrodes, namely a distal electrode 16 and a proximal electrode 18, thereby collecting a first electrogram $V_{bip}$ corresponding to the potential difference measured between the distal electrode 16 and the proximal electrode 18, and second electrogram $V_{uni}$, measured by the potential difference between one of the electrodes, for example the proximal electrode 18 and the metal casing of the generator 10. An atrial lead 19, provided with distal and proximal detection electrodes 20, 21 is placed in the right atrium 22 for the detection of signals in this cavity and can be used for the application of an atrial stimulation.

In the case of biventricular pacing (e.g., for restoring synchronization between the two ventricles), the device is provided with a second ventricular lead 24, for example a lead disposed in the coronary network, having an electrode 26 disposed near the left ventricle 28. This left ventricular electrode 26 can be used to provide for the simultaneous stimulation of both the right and left ventricles to restore synchronization between the two cavities and enhance the systemic hemodynamic of the patient.

Note that in the case of a defibrillator, the bipolar signal $V_{bip}$ can also be collected from one of the electrodes 16 and 18 and the ventricular coil forming a defibrillation electrode, the unipolar signal $V_{uni}$ then being collected between the metallic housing 10 and this ventricular coil.

Figure 2:
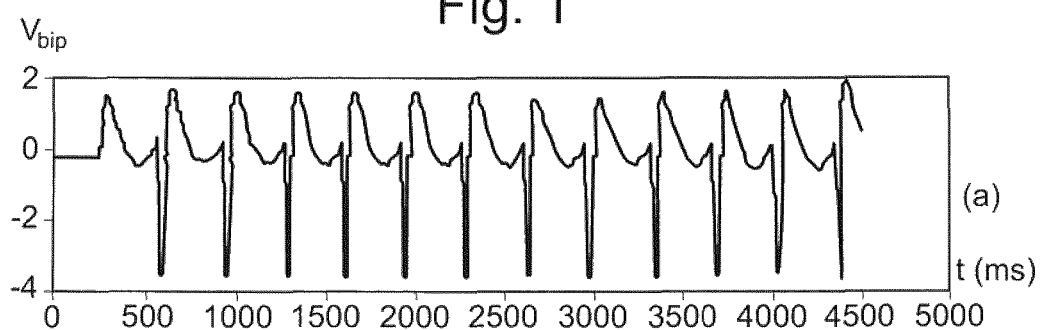
FIG. 2 illustrates the EGM signals respectively obtained on the ventricular bipolar and unipolar channels of the lead of FIG. 1, according to an exemplary embodiment.
Figure 2:
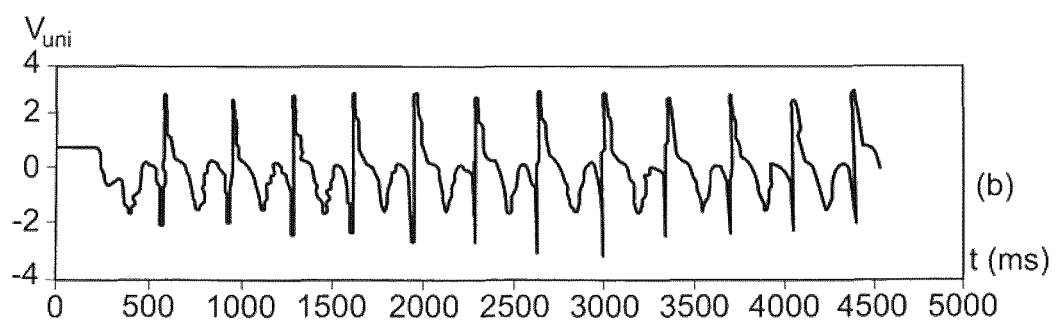

FIG. 2 shows an example of $V_{bip}$ and $V_{uni}$ electrogram plots observed respectively on the ventricular bipolar channel (FIG. 2a) and on the ventricular unipolar channel (FIG. 2b) of the configuration of FIG. 1.

Figure 3:
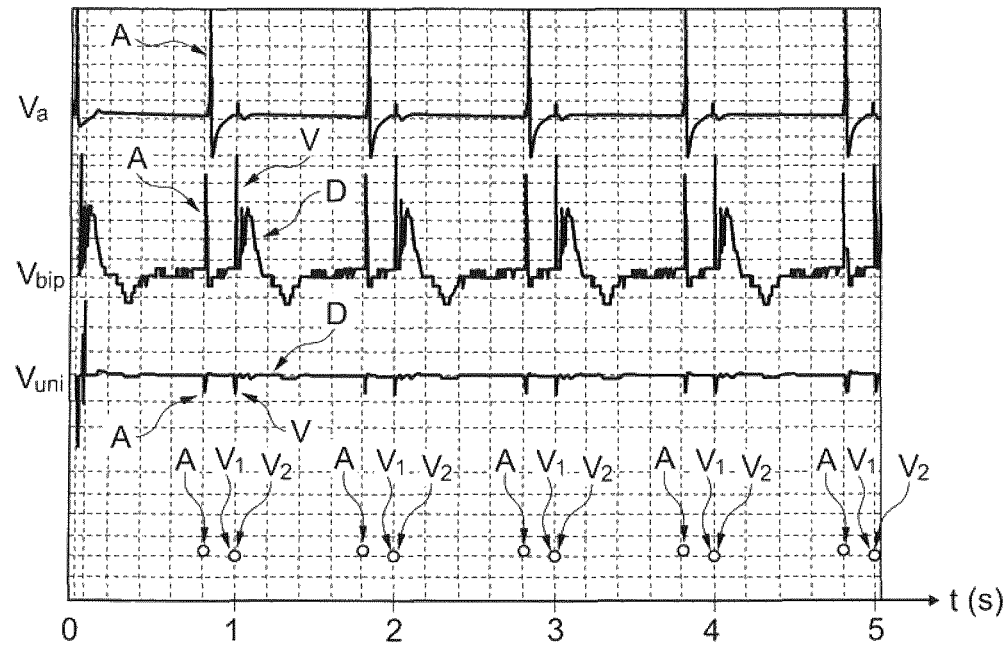
FIG. 3 is an example of EGM signals obtained in a configuration of biventricular pacing, showing the prevalence of the bipolar signal with respect to the unipolar signal.

FIG. 3 is an example of EGM signals obtained in a configuration of biventricular pacing, showing the predominance of the bipolar signal $V_{bip}$ compared to the unipolar signal $V_{uni}$. In this figure, the timing diagrams of the ventricular EGM signals $V_{bip}$ and $V_{uni}$ are shown, as well as the atrial EGM signal $V_a$. In addition, markers A and $V_1$, $V_2$ indicate the moments of application of atrial and ventricular pacing stimuli (in this example, concurrent for both the right and left ventricles). Five cycles are visible, all corresponding to capturing stimulation. In examining this figure, it should be noted that the far-field EGM signal of unipolar component $V_{uni}$ includes an atrial stimulation peak A, a ventricular stimulation peak V and a depolarization D. However, this depolarization D is virtually nonexistent on the $V_{uni}$ signal, so that a discrimination algorithm based solely on the depolarization signal level would consider—wrongly—that there has been loss of capture. However, the near-field EGM signal of bipolar component $V_{bip}$ presents a correct resolution (amplitude of about 2 V of the depolarization D), and would be sufficient to determine the actual presence of a capture.

Figure 4:
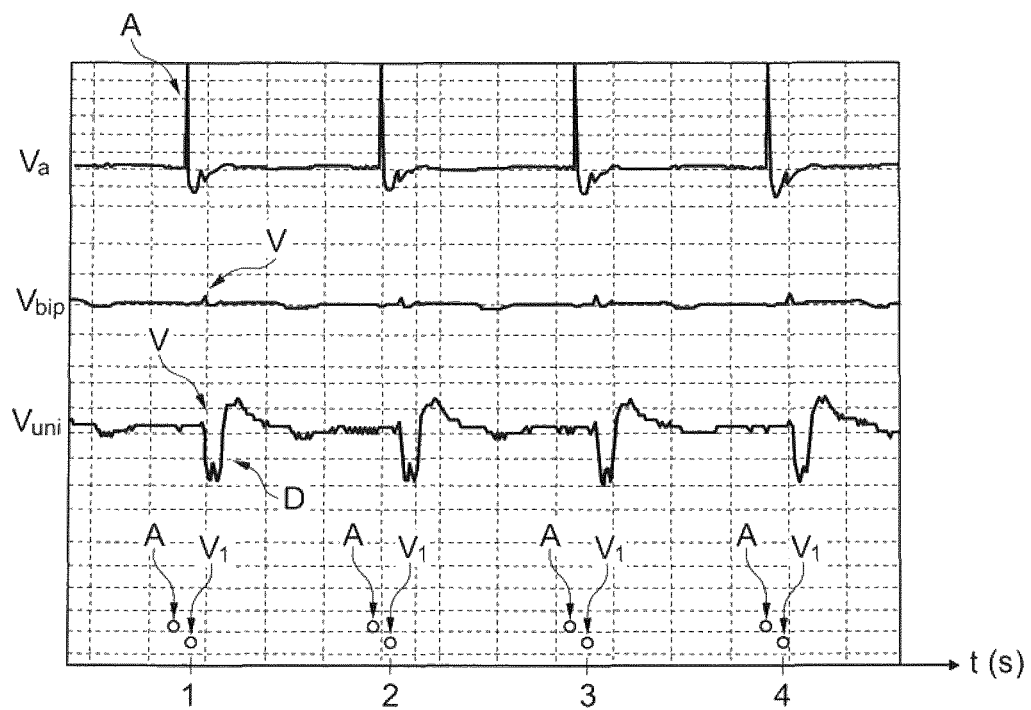
FIG. 4 is an example of EGM signals obtained in a configuration of the right ventricular stimulation only, showing the prevalence of the unipolar signal with respect to the bipolar signal.

FIG. 4 is another example of EGM signals obtained in a stimulation configuration of only the right ventricle, showing the prevalence of the unipolar signal $V_{uni}$ compared to the bipolar signal $V_{bip}$. The four visible cycles on these timing diagrams all correspond to capturing stimulations. However, the situation is opposite to that of the example in FIG. 3: it can indeed be observed that the ventricular depolarization on the $V_{bip}$ signal is of very low amplitude and width (less than 1 V), which could mislead a capture discrimination algorithm based on the analysis of this signal. In contrast, the $V_{uni}$ signal has a sufficient quality and amplitude at the depolarization D to be properly interpreted by the algorithm, which would prove the presence of a capture.

As illustrated in FIGS. 3 and 4, therefore, the use of a single EGM channel, $V_{bip}$ or $V_{uni}$, to verify the capture on a stimulated cycle can lead to errors in the assessment of the presence or loss of capture, especially when the EGM is of poor quality.

Figure 5:
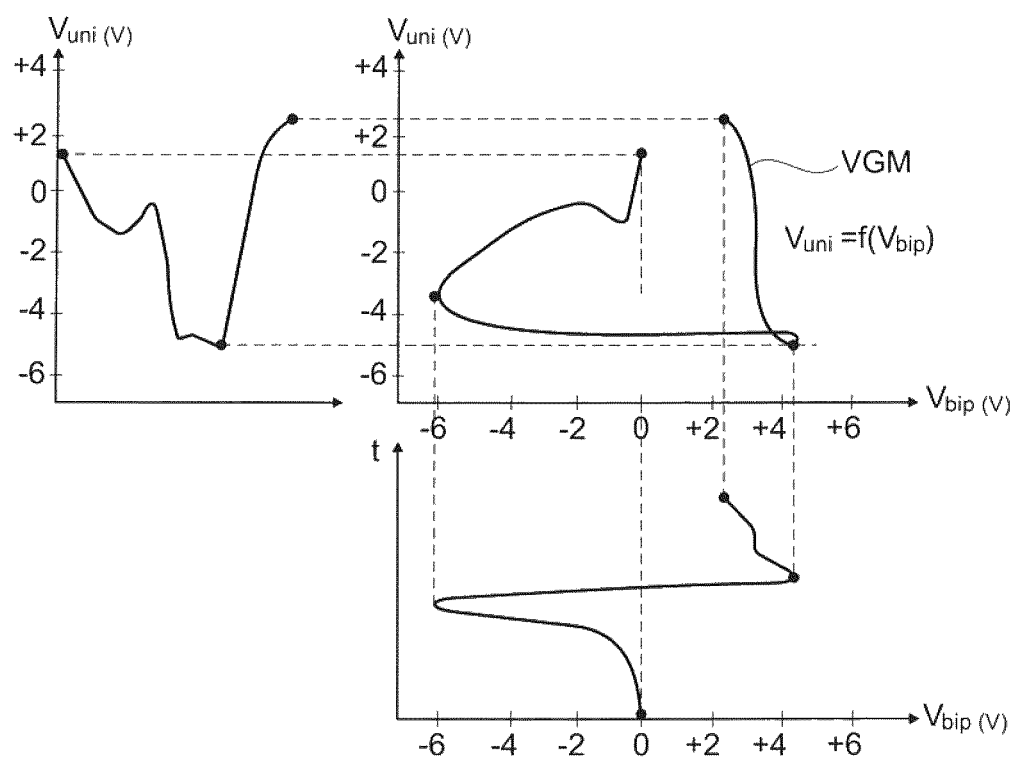
FIG. 5 illustrates the method for combining the unipolar and bipolar signals in FIG. 2 to obtain a 2D vectogram characteristic (VGM).

Systems and methods of the present invention can advantageously overcome this problem, by collecting at least two distinct temporal components (in this case, the EGM signals, $V_{bip}$ and $V_{uni}$) from the same cavity, usually the right ventricle. Both temporal components $V_{bip}$ and $V_{uni}$ are illustrated in FIG. 5. FIG. 5 illustrates a method to combine the two temporal components $V_{bip}$ and $V_{uni}$ to obtain a vectogram 2D characteristic (VGM). Specifically, the collected $V_{uni}(t)$ and $V_{bip}(t)$ EGM signals are sampled and the successive samples of the two components thus collected are stored and combined to eliminate the temporal variable t and to produce a parametric curve (VGM vectogram) $V_{uni}=f(V_{bip})$.

The curve $V_{uni}=f(V_{bip})$ is a parametric curve without temporal dimension, plotted from the variations of one of the temporal components ($V_{uni}$) versus the other ($V_{bip}$).

The curve results in a vectocardiogram characteristic (VGM) representative of the cardiac cycle (or of a fraction of this cycle) to be analyzed, and can be referred to as a "non-temporal 2D characteristic." It graphically has the form of a loop, and time is only present in the manner by which the loop is traveled on the cycle duration or on the fraction of the cycle. In other words, time may be present in the ordering of the $V_{bip}$ and $V_{uni}$ pairs.

Incidentally note that the "bidimensional" or "two-dimensional" (2D) evoked here should not be understood in a limited manner. The invention may indeed apply to both analysis in a higher multidimensional space (3D or more). For example, there may be embodiments wherein EGM signals from a single cavity are collected simultaneously on three or more channels.

Moreover, in certain embodiments it is not necessary to analyze the entire cycle. Rather, the analysis of a fraction of the cycle (e.g., typically that beginning at the instant of the stimulation, or that centered on the QRS complex, etc.) may be sufficient to provide accurate detection of the evoked wave and to discriminate between the capturing cycle and non-capturing cycle.

As illustrated in the Figures, the representative curvilinear characteristic of the VGM is not a closed loop. Rather, it is only a part of the complete cardiac loop, namely the QRS complex isolated within a given analysis window.

Figure 6:
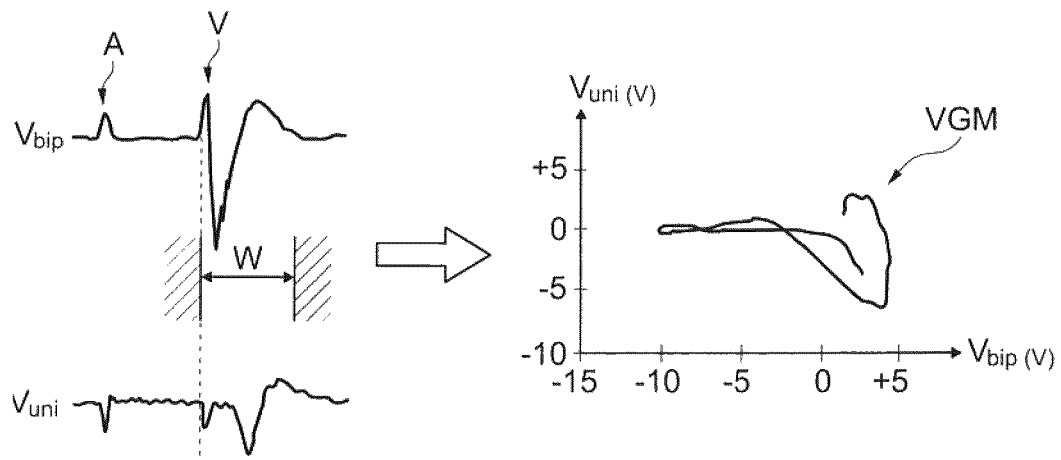
FIG. 6 is an example of a vectogram obtained from EGMs from the same cavity wherein stimulation is applied.
Figure 7:
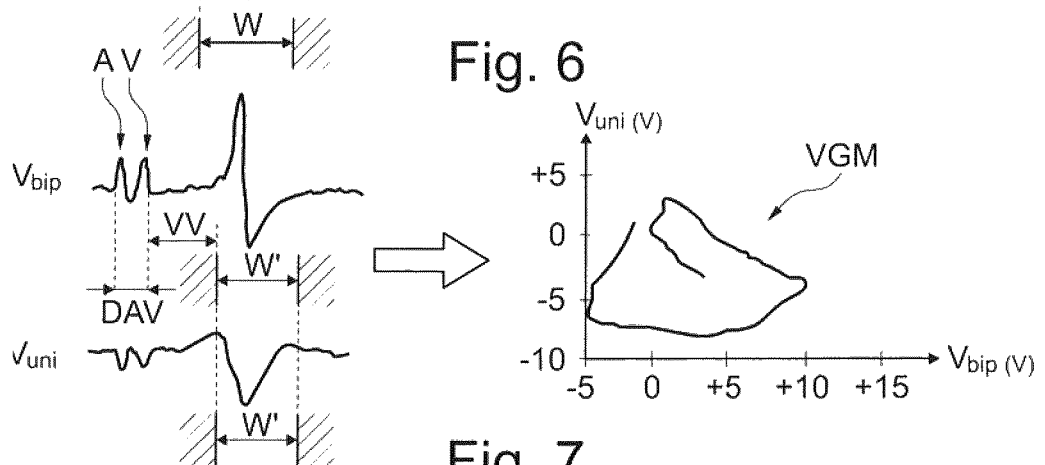
FIG. 7 is an example of a vectogram obtained from EGMs from another cavity than that wherein stimulation is applied.

FIGS. 6 and 7 may be examples of vectograms obtained from EGM respectively collected from the same cavity than that wherein the stimulation is applied, and from another cavity than that wherein the stimulation is applied. In other words, varying embodiments may consider the $V_{uni}$ and $V_{bip}$ EGMs of the stimulated cavity, or either the $V_{uni}$ and $V_{bip}$ EGMs from another cavity.

FIG. 6 illustrates the case wherein the EGMs are from the same cavity as the stimulation. In the example of FIG. 6, the samples used to plot the VGM are selected in a window W, of e.g., 63 ms from the moment V of the ventricular pacing (the beginning of this window being optionally shifted, up to 30 ms, if it is desirable to avoid considering the actual stimulation peak V).

FIG. 7 corresponds to another case, wherein the $V_{bip}$ and $V_{uni}$ EGMs are originated from another cavity that that wherein the stimulation takes place. In this example, the points used are selected in a window W', for example of 63 ms, centered on the depolarization wave. The window is centered on the depolarization wave corresponding to a stimulated cycle that has a proven capture. This window may be the same during all the capture tests. Given the size of the window, in the case of loss of capture, the window will not contain any depolarization (stimulated or natural) because the spontaneous or natural depolarization come later, after the end of the window.

When stimulation is performed concurrently in two cavities, typically in the case of biventricular pacing, the delay between two ventricular stimulations is generally low, or zero, so that the stimulation of a cavity will not be carried out in the second cavity. In such a case, the $V_{bip}$ and $V_{uni}$ EGMs of a first cavity may be used as the basis to determine whether the stimulation in this cavity was capturing or not, and similarly for the second cavity. However, if the delay between stimulation of the two cavities is important and the stimulation of a first cavity is carried out in the other cavity before the stimulation of the latter cavity occurs, the capture test may be conducted on the single stimulation in the first cavity. The device may be configured such that, in case of loss of capture, the natural cycle does not appear in the window used to trace the VGM characteristic to make a capture determination. To accomplish this, the device may use a short atrioventricular delay (AVD) during the capture test. However, this modification may not be sufficient in particular in the case wherein the EGM signals are originated from another cavity than that wherein the stimulation occurred: there is thus a delay between the moment of stimulation in a first cavity (one of the ventricles) and that of the depolarization observed on the $V_{bip}$ and $V_{uni}$ EGM signals of the second cavity (the other ventricle).

As noted above, the window used to plot the VGM representation is centered on the depolarization corresponding to a capturing stimulation. To ensure that no spontaneous depolarization is present in this window, in addition to temporary shortening of the programmed AVD, the system may start the capture test, that the following condition is satisfied (in the assumption that both cavities are ventricles): AR (or PR)≥DAV+VV+M. AR (or PR) being the interval between the atrial stimulus (or detection) of the subsequent ventricular depolarization, DAV being the duration of the atrioventricular delay, VV being the conduction delay between the two cavities, that is to say the time it takes for the depolarization from a stimulation of a cavity to propagate and be detectable in the not stimulated cavity, and M being a constant corresponding to the permissible minimum difference between DAV+VV and AR (or PR), for example M=63 ms. The window centered on the depolarization is a window that begins at an instant located defined by DAV+VV from atrial depolarization A (or P) and ending at (DAV+VV+63 ms), as shown in FIG. 7. This window size and position may help ensure that the presence of a depolarization will accurately indicate effective capture, while the absence of depolarization will accurately indicate a loss of capture.

Figures 8A, 8B:
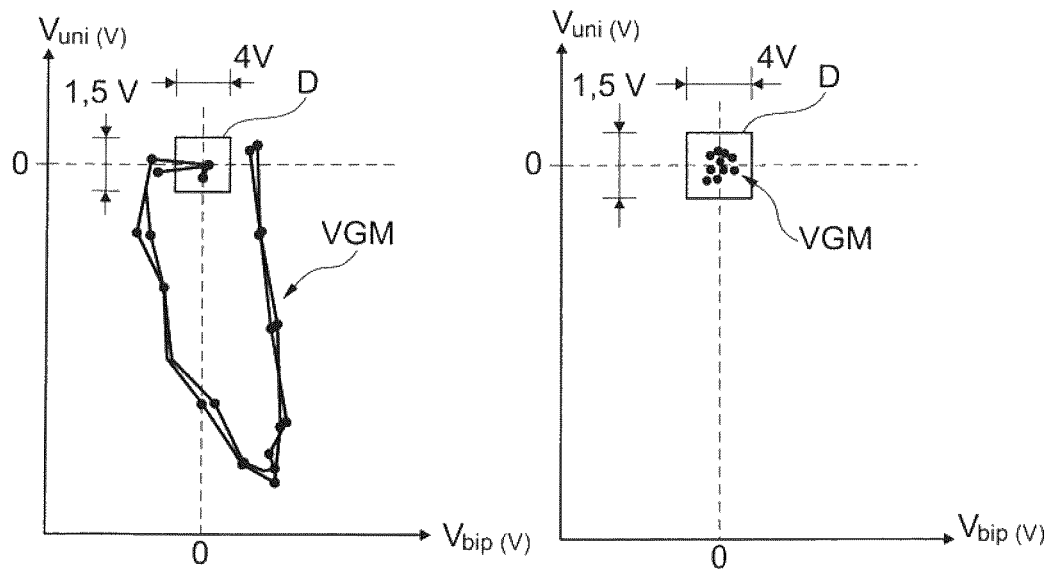
FIGS. 8a and 8b show the vectograms obtained respectively in the presence and absence of a capture, wherein the devices and methods of the invention can discriminate between these two situations by a topological analysis of the vectogram.

If visualized, the VGM characteristic determined by the successive sampling points of the $V_{bip}$ and $V_{uni}$ signals has the appearance of a curve, as shown in FIG. 8*a* (an open curve if the sampling is done on only a fraction of the cardiac cycle). In contrast, in case of a loss of capture, the VGM characteristic simply consists of a cloud of points centered roughly around the point with coordinates {0,0}, as shown in FIG. 8*b*. According to embodiments of the present application, a domain D is defined relative to a VGM characteristic field of $\{V_{bip}\}$ pairs. The domain D may be caused to overlay this field to assess whether a particular VGM characteristic or series of characteristics is contained or not in the domain, and to decide whether there is the presence or absence of a capture.

The domain D can be, as shown FIGS. 8*a* and 8*b*, a rectangular domain centered on the point of coordinates {0,0}, with side dimensions of 4V (for $V_{bip}$) and 1.5V (for $V_{uni}$). The decision criterion is for example the following:—If all the points of the VGM characteristic are inside this rectangle, then there is no capture; —If at least one point of the characteristic is outside of the rectangle, then there is capture.

Different criteria can be used to test for capture relative to the domain D. For example, a capture test may require the presence of at least two points of the VGM characteristic outside the rectangle to determine the presence of capture. In another embodiment two consecutive points must be present outside this rectangle. Such a "two consecutive points" test may help detect capture even if a point, for example, of the stimulation peak is within the analysis temporal window.

The systems and methods of the present disclosure advantageously present an effective method to discriminate between capturing and non-capturing stimulation, without implementing complex morphological analysis techniques of the VGM characteristic, and without comparison of this characteristic to reference models previously acquired and requiring regular updating.

The capture test may be performed cycle-to-cycle, or be made at regular intervals, for example every six hours. The capture test result can notably be used to verify that a particular therapy has been successfully delivered to the various stimulated sites, particularly in the case of a CRT therapy wherein it may be essential that both ventricles are stimulated jointly and/or to adapt if necessary the pacing intervals (atrioventricular delay AVD and/or interventricular delay VVD) based on the results.

The capture test described herein can also be used to determine the stimulation threshold and to adjust the amplitude of the stimulation pulse. To accomplish this, the device may apply to the cavity stimulation pulses of decreasing energy. If at a given energy capture is confirmed, the device may consider that the stimulation to be an effective stimulation. The energy applied for the next stimulation can be reduced (e.g., by a fixed amplitude of 0.25 V). Once the capture is lost, then the device can then consider the stimulation is ineffective. The stimulation amplitude can then be adjusted to be larger than the last applied value. The stimulation threshold thus determined can be stored in the device memory, can be transmitted to a data collection center, or can be used by the implant to adjust the stimulation amplitude.

For further details on the stimulation amplitude adjustment algorithms from successive capture tests, reference may be made in particular to EP1080744A1 (ELA Medical), which describes various techniques for measuring the threshold, for measurement consistency check and for adjusting the width and amplitude of the stimulation pulse. The adjustment algorithms described in EP1080744A1 can be implemented with a capture test performed from an analysis of the VGM characteristic as described in the present application.

The invention claimed is:

1. An active medical device, comprising:
   a stimulator coupled to a first lead configured to deliver electrical stimulation pulses to at least one heart chamber of a patient; and
   a circuit for collecting the electrical activity of the heart, wherein the circuit generates at least two distinct readings from two separate endocardial electrogram signals concurrently collected, wherein the circuit is configured to perform a capture test to detect the occurrence of a depolarization wave induced by the stimulation of the heart chamber, wherein the circuit performs the capture test by determining a non-temporal two dimensional characteristic representative of the cardiac cycle to be analyzed by pairing the variations of the two distinct readings from the two separate endocardial electrogram signals, wherein the capture test comprises determining whether the non-temporal two-dimensional characteristic is contained within a predetermined two dimensional domain.

2. The device of claim 1, wherein the domain is a rectangular domain.

3. The device of claim 2, wherein the domain is centered on the point of origin of the space for the two temporal components.

4. The device of claim 1, wherein the non-temporal two dimensional characteristic is a sampled two dimensional characteristic described by a series of successive discrete points, and wherein the capture test comprises comparing the position of each point to the domain.

5. The device of claim 1, wherein the capture test determines a presence of capture when at least one point of the sampled two dimensional characteristic is outside the domain.

6. The device of claim 1, wherein the capture test determines a presence of capture when two consecutive points of the sampled two dimensional characteristic are outside of the domain.

7. The device of claim 1, wherein the circuit defines a time window for collecting the endocardial electrogram signals and wherein the time window is started and stopped to avoid capturing a depolarization wave associated with a spontaneous contraction.

8. The device of claim 1, wherein the circuit is configured to temporarily shorten an atrioventricular delay during the activation of the capture test to increase the chances that a spontaneous ventricular contraction occurring after an absence of capture is outside the temporal analysis window.

9. The device of claim 1, wherein the endocardial electrogram signals concurrently collected on separate respective channels include:
   a near-field signal of bipolar component ($V_{bip}$) collected between a proximal electrode and a distal electrode of a lead adapted to be placed in a cardiac cavity; and
   a far-field signal of unipolar component ($V_{uni}$) collected between the housing of the device and the proximal or distal electrode of the lead.

10. A computerized method for monitoring effective electrical stimulation of a tissue, comprising:
    simultaneously collecting data for at least two electrical signals using electrodes separately located relative to the tissue;
    creating a series of pairs by temporally matching the data for the at least two electrical signals; and
    evaluating the series of pairs relative to a boundary defining a two dimensional area, wherein the evaluation comprises determining whether the series of pairs are contained within the boundary, and outputting a presence of capture in response to the evaluation.

11. The method of claim 10, wherein the tissue is the heart, the electrodes are on intracardiac leads, and wherein the computerized method is executed by an active implantable medical device configured to monitor stimulation of the heart.

12. The method of claim 11, wherein the at least two electrical signals comprise two separate endocardial electrogram (EGM) signals.

13. The method of claim 12, wherein the two separate EGM signals comprise:
    (a) a unipolar signal representing a far-field voltage between the housing of the implantable medical device and an electrode; and
    (b) a bipolar signal representing a near-field voltage between a first electrode and a second electrode.

14. The method of claim 13, wherein the electrode used to collect the unipolar signal is one of the first electrode and the second electrode.

15. The method of claim 10, wherein the two dimensional area would be a rectangular area of predefined size and position relative to the series of pairs if plotted.

16. The method of claim 15, wherein the evaluation comprises a topological analysis of the distribution of the series of pairs relative to the area.

17. A method for discriminating between stimulation capture and the lack of stimulation capture, comprising:
    producing at least two distinct temporal readings from two separate endocardial electrogram (EGM) signals concurrently collected;
    determining a vectogram representative of the cardiac cycle by creating pairs of the readings;
    defining a two dimensional threshold range relative to the vectogram; and
    outputting the presence of capture based on determining whether the vectogram is contained within the two dimensional threshold range.

18. The method of claim 17, wherein the comparison between the two dimensional threshold range to the vectogram to output the presence of capture is completed without analyzing the shape of the vectogram.

19. The method of claim 17, wherein the comparison between the two dimensional threshold range to the vectogram to output the presence of capture is completed without analyzing the vectogram relative to a reference vectogram.

20. The method of claim 17, wherein the two dimensional threshold range is defined as a rectangular area relative to the vectogram.

* * * * *